(12) United States Patent
Walsh et al.

(10) Patent No.: US 10,357,387 B2
(45) Date of Patent: Jul. 23, 2019

(54) MEDICAL DEVICES FOR USE ALONG THE BILIARY AND/OR PANCREATIC TRACT

(71) Applicant: BOSTON SCIENTIFIC SCIMED, INC., Maple Grove, MN (US)

(72) Inventors: Kevin Walsh, Wellesly, MA (US); John Petricca, Ashland, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 120 days.

(21) Appl. No.: 15/599,960

(22) Filed: May 19, 2017

(65) Prior Publication Data

US 2017/0252189 A1    Sep. 7, 2017

Related U.S. Application Data

(63) Continuation of application No. 15/370,430, filed on Dec. 6, 2016, which is a continuation of application
(Continued)

(51) Int. Cl.
| | | |
|---|---|---|
| *A61F 2/04* | (2013.01) |
| *A61F 2/90* | (2013.01) |
| *A61F 2/82* | (2013.01) |
| *A61F 2/07* | (2013.01) |
| *A61B 1/273* | (2006.01) |
| *A61F 2/91* | (2013.01) |
| *A61M 27/00* | (2006.01) |

(52) U.S. Cl.
CPC ............... *A61F 2/90* (2013.01); *A61B 1/273* (2013.01); *A61F 2/04* (2013.01); *A61F 2/07* (2013.01); *A61F 2/82* (2013.01); *A61F 2/91* (2013.01); *A61M 27/002* (2013.01); *A61F 2002/041* (2013.01); *A61F 2002/045* (2013.01); *A61F 2002/821* (2013.01); *A61F 2210/009* (2013.01); *A61F 2210/0014* (2013.01); *A61F 2210/0076* (2013.01); *A61F 2210/0095* (2013.01); *A61F 2230/0013* (2013.01); *A61F 2230/0019* (2013.01); *A61F 2230/0023* (2013.01);
(Continued)

(58) Field of Classification Search
CPC ......... A61F 2/04; A61F 2002/041; A61F 2/90
See application file for complete search history.

(56) References Cited

U.S. PATENT DOCUMENTS 5,238,004 A    8/1993 Suhatjian et al.
5,645,559 A    7/1997 Hachtman et al.
(Continued)

FOREIGN PATENT DOCUMENTS

| CN | 201108514 Y | 9/2008 |
| CN | 201684049 U | 12/2010 |
| WO | 2008076706 A2 | 6/2008 |

*Primary Examiner* — Suba Ganesan
(74) *Attorney, Agent, or Firm* — Seager, Tufte & Wickhem, LLP

(57) ABSTRACT

Medical devices and method for making and using the same are disclosed. An example medical device may include implantable medical device for use along the biliary and/or pancreatic tract. The implantable medical device may include a tubular member having a first end configured to be disposed within the duodenum of a patient and a second end configured to be disposed adjacent to a pancreatic duct and/or bile duct. The tubular member may have a body including one or more wire filaments that are woven together. The tubular member may also have an outer surface with a longitudinal channel formed therein.

16 Claims, 11 Drawing Sheets

Related U.S. Application Data

No. 15/055,516, filed on Feb. 26, 2016, now Pat. No. 9,675,475, which is a continuation of application No. 14/192,660, filed on Feb. 27, 2014, now Pat. No. 9,539,126.

(60) Provisional application No. 61/770,367, filed on Feb. 28, 2013.

(52) U.S. Cl.
CPC ............ *A61F 2310/00017* (2013.01); *A61F 2310/00023* (2013.01); *A61F 2310/00029* (2013.01); *A61F 2310/00059* (2013.01); *A61F 2310/00077* (2013.01); *A61F 2310/00101* (2013.01); *A61F 2310/00137* (2013.01); *A61F 2310/00149* (2013.01); *A61M 2210/1021* (2013.01)

(56) References Cited

U.S. PATENT DOCUMENTS

| | | | |
|---|---|---|---|
| 6,508,803 B1 | 1/2003 | Horikawa et al. | |
| 7,169,139 B2 | 1/2007 | Teague et al. | |
| 8,454,675 B2 | 6/2013 | Houston et al. | |
| 8,753,407 B2 * | 6/2014 | Nguyen | A61F 2/04 623/1.13 |
| 2002/0179166 A1 | 12/2002 | Houston et al. | |
| 2003/0040771 A1 | 2/2003 | Hyodoh et al. | |
| 2003/0191517 A1 | 10/2003 | Osborne et al. | |
| 2004/0039435 A1 | 2/2004 | Hancock et al. | |
| 2004/0127973 A1 | 7/2004 | Mangiardi et al. | |
| 2005/0154448 A1 * | 7/2005 | Cully | A61F 2/07 623/1.15 |
| 2005/0240278 A1 | 10/2005 | Aliski et al. | |
| 2007/0123969 A1 * | 5/2007 | Gianotti | A61F 2/90 623/1.2 |
| 2007/0282453 A1 | 12/2007 | Weitzner et al. | |
| 2007/0299506 A1 | 12/2007 | Carter et al. | |
| 2009/0138070 A1 | 5/2009 | Holzer et al. | |
| 2010/0030321 A1 | 2/2010 | Mach | |
| 2010/0100170 A1 | 4/2010 | Tan et al. | |
| 2010/0256731 A1 | 10/2010 | Mangiardi | |
| 2011/0213453 A1 * | 9/2011 | Mangiardi | A61F 2/82 623/1.11 |
| 2012/0116528 A1 | 5/2012 | Nguyen | |
| 2012/0165956 A1 | 6/2012 | Li | |
| 2012/0290100 A1 | 11/2012 | Li | |
| 2012/0296257 A1 | 11/2012 | Van Dam et al. | |

* cited by examiner

MEDICAL DEVICES FOR USE ALONG THE BILIARY AND/OR PANCREATIC TRACT

CROSS-REFERENCE TO RELATED APPLICATIONS

This application is a continuation of U.S. application Ser. No. 15/370,430, filed Dec. 6, 2016, which is a continuation of U.S. application Ser. No. 15/055,516, filed Feb. 26, 2016, which is a continuation of U.S. application Ser. No. 14/192,660, filed Feb. 27, 2014, now U.S. Pat. No. 9,539,126, which claims priority under 35 U.S.C. § 119 to U.S. Provisional Application Ser. No. 61/770,367, filed Feb. 28, 2013, the contents of which are incorporated herein by reference.

TECHNICAL FIELD

The present disclosure pertains to medical devices, and methods for manufacturing medical devices. More particularly, the present disclosure pertains to medical devices for draining body fluids along the pancreatic and/or biliary tract.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include implantable medical device for use along the biliary and/or pancreatic tract. The implantable medical device may include a tubular member having a first end configured to be disposed within the duodenum of a patient and a second end configured to be disposed adjacent to a pancreatic duct and/or bile duct. The tubular member may have a body including one or more wire filaments that are woven together. The tubular member may also have an outer surface with a longitudinal channel formed therein.

Another example implantable medical device for use along the pancreatic tract may include a braided stent having a first end configured to be disposed within the duodenum of a patient and a second end configured to be disposed adjacent to a pancreatic duct so as to drain fluid. The braided stent may have an outer surface with a longitudinal channel formed therein. The longitudinal channel may be configured to drain fluid from branches of the pancreatic duct.

An example method for draining fluids along the biliary and/or pancreatic tract may include providing an implantable medical device. The implantable medical device may include a braided stent having a first end configured and a second end. The braided stent may have an outer surface with a longitudinal channel formed therein. The method may also include disposing the braided stent within a patient such that the first end is disposed within the duodenum and the second end extends within a region of the biliary and/or pancreatic tract, and draining fluid from the region of the biliary and/or pancreatic tract.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
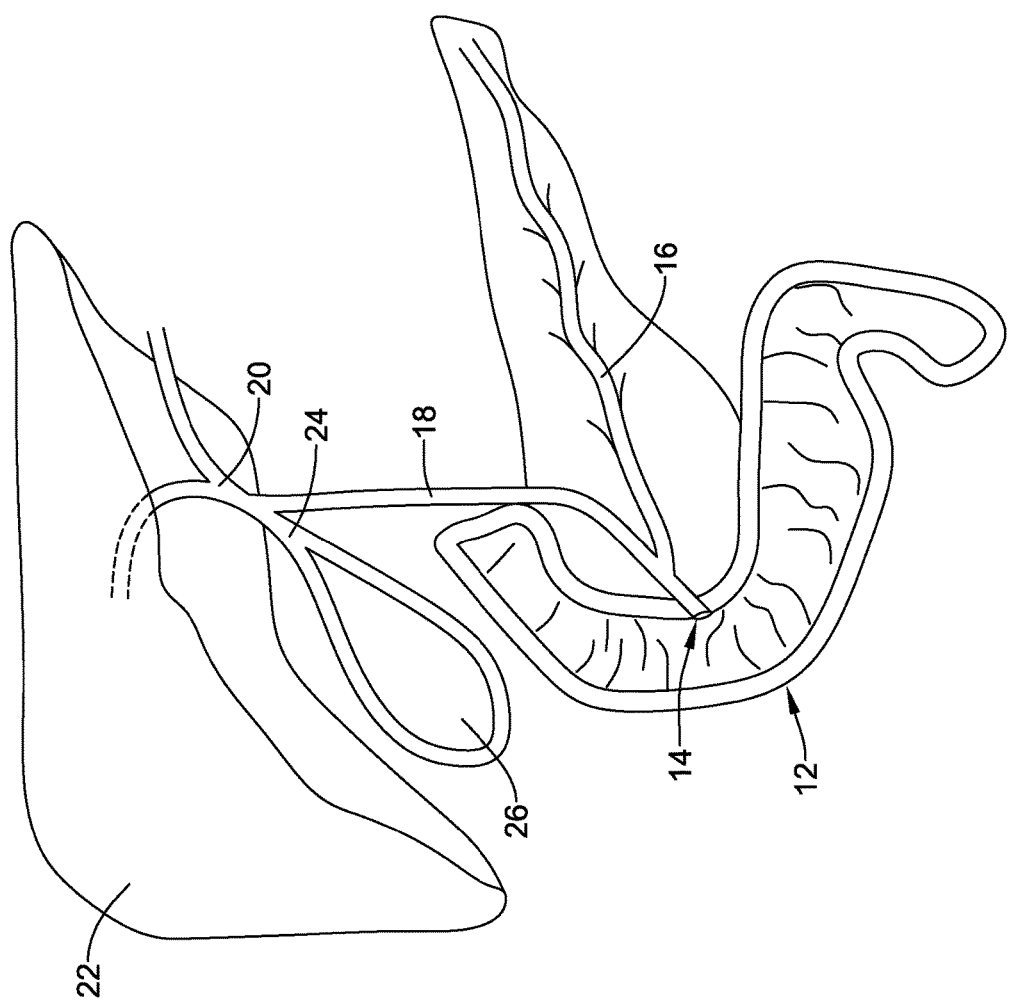
FIG. 1 is a schematic overview of the biliary and/or pancreatic tree.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Embodiments of the present disclosure relate to medical devices and procedures for to accessing body lumens, and specifically, for draining fluids from the pancreatic duct and/or the bile duct of the biliary tree in a patient's body.

Endoscopic retrograde cholangiopancreatography (ERCP) is primarily used to diagnose and treat conditions of the bile ducts, including, for example, gallstones, inflammatory strictures, leaks (e.g., from trauma, surgery, etc.), and cancer. Through the endoscope, the physician can see the inside of the stomach and the duodenum, and inject dies into the ducts in the bile tree and pancreas so they can be seen on X-rays. These procedures may necessitate gaining and keeping access to the biliary duct, which may be technically challenging, may require extensive training and practice to gain proficiency, and may require one or more expensive tools in order to perform. Blockage of the biliary duct may occur in many of the disorders of the biliary system, including the disorders of the liver, such as, primary schlerosing cholangitis, stone formation, scarring in the duct, etc. This requires the need to drain blocked fluids from the biliary system, to treat the disorders. In many cases, the clinician places a fine needle through the skin of the abdomen and into the liver, advancing it into the bile duct. A drainage tube is then placed in the bile duct, which drains the blocked fluids out of the biliary system.

During an ERCP procedure, a number of steps are typically performed while the patient is often sedated and anaesthetized. For example, an endoscope may be inserted through the mouth, down the esophagus, into the stomach, through the pylorus into the duodenum, to a position at or near the ampulla of Vater (the opening of the common bile duct and pancreatic duct). Due to the shape of the ampulla, and the angle at which the common bile and pancreatic ducts meet the wall of the duodenum, the distal end of the endoscope is generally placed just past the ampulla. Due to positioning of the endoscope beyond the ampulla, the endoscopes used in these procedures are usually side-viewing endoscopes. The side-viewing feature provides imaging along the lateral aspect of the tip rather than from the end of the endoscope. This allows the clinician to obtain an image of the medical wall of the duodenum, where the ampulla of Vater is located, even though the distal tip of the endoscope is beyond the opening.

FIG. 1 illustrates an overview of the biliary system or tree. The ampulla of Vater is located at the illustrated portion of the duodenum 12. For the purpose of this disclosure, the ampulla of Vater 14 is understood to be of the same anatomical structure as the papilla of Vater. The ampulla of Vater 14 generally forms the opening where the pancreatic duct 16 and the bile duct 18 can empty into the duodenum 12. The hepatic ducts, denoted by the reference numeral 20, are connected to the liver 22 and empty into the bile duct 18. Similarly, the cystic duct 24, being connected to the gall bladder 26, also empties into the bile duct 18. In general, an endoscopic or biliary procedure may include advancing a medical device to a suitable location along the biliary tree and then performing the appropriate intervention.

Accessing a target along the biliary tree may often involve advancing an endoscope through the duodenum 12 to a position adjacent to the ampulla of Vater 14, and advancing a medical device, which may be a stent, through the endoscope and through the ampulla of Vater 14 to the intended target. The intended target may be, for example, the common bile duct 18 and the pancreatic duct 16.

The present disclosure provides devices and methods for improving access to various target locations along the biliary tree, and to drain fluids along a target location within the biliary tree of a patient's body. For example, these systems and methods may allow a medical device, such as a stent, to easily access a particular target location along the biliary and/or pancreatic tree and to drain a fluid from a target location. Furthermore, the systems and methods may allow a clinician to access a target location, without the need to re-cannulate the ampulla of Vater 14, the common bile duct 18, and/or the pancreatic duct 16. In addition, some portions of the biliary and/or pancreatic tree (e.g., the pancreatic duct) may be relatively highly branched. Some drainage stents may have a tendency to cover or other obstruct one or more of the branches. At least some of the devices and methods disclosed herein may include structural features that are designed to help provide drainage of both the main duct as well as drainage along one or more branches off of the main duct.

Figure 2:
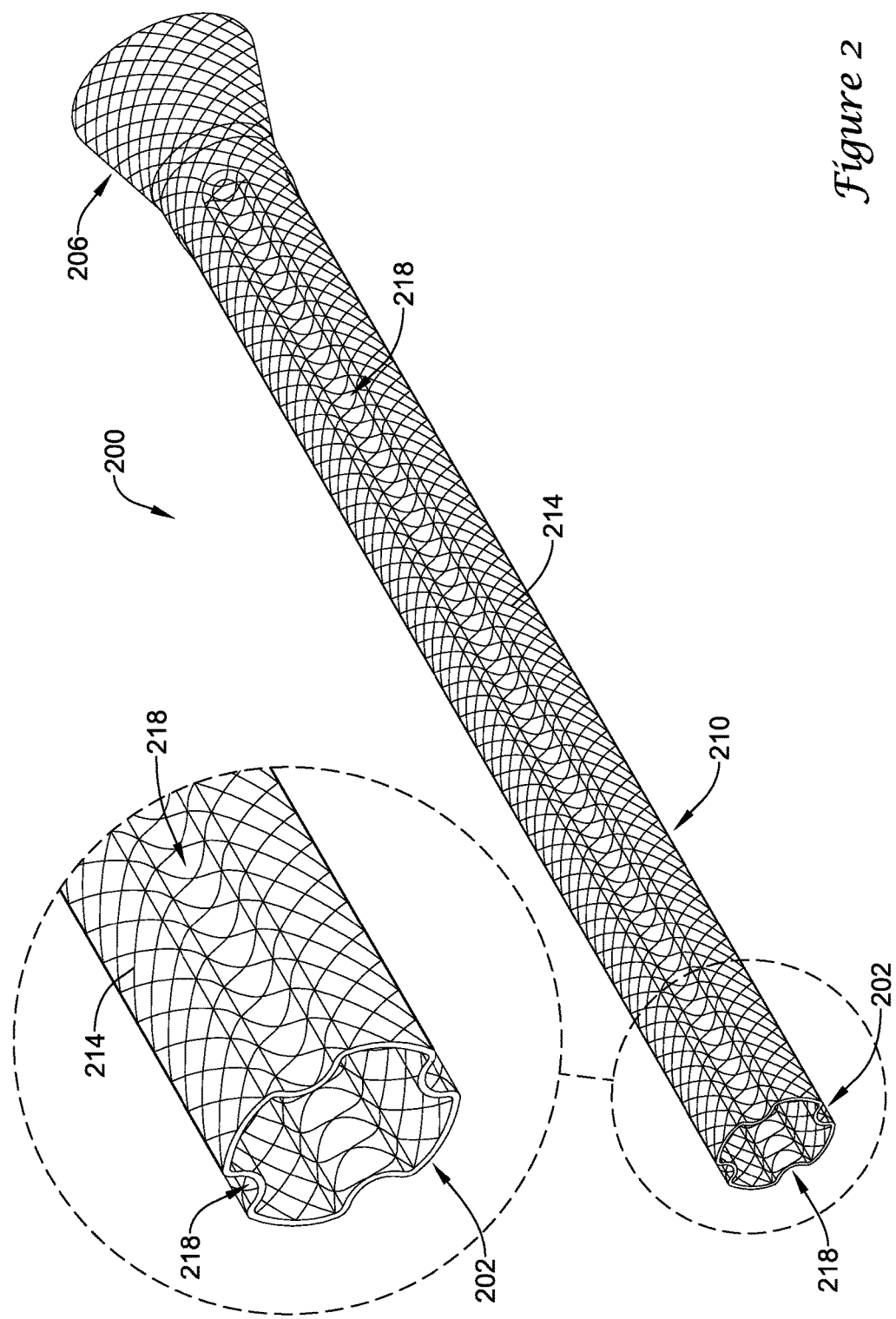
FIG. 2 is a perspective view of an example stent configured to drain fluids along the biliary and/or pancreatic tract of a patient's body.

FIG. 2 illustrates a portion of an implantable medical device 200 configured to be disposed along the biliary and/or pancreatic tree of a patient's body. As shown in FIG. 2, the implantable medical device 200 includes may take the form of a stent 200. The stent 200 may vary in form. In general, the stent 200 may be configured as a drainage stent. In some embodiments, the stent 200 may be a braided or mesh tube and may be configured to be inserted into a lumen of the biliary and/or pancreatic tree. In general, a first end 206 of the stent 200 may be flared and may be configured to be positioned into the duodenum of the patient's body. Further, a second end 202 of the stent 200 is configured to be positioned into/adjacent to the pancreatic duct or the biliary duct of the patient's body. A central lumen may be defined in the stent 200 that may be utilized to drain fluids from the pancreatic duct or the biliary duct.

The stent 200 may have a stent body 210 formed from one or more wire filaments 214. The wire filaments 214 may be wound in a manner that they interlace each other. In some embodiments, a single wire filament 214 may be used to define the stent body 210. Alternatively, a plurality of wire filaments 214 may be used to define the stent body 210. The single or plurality of wire filaments 214 may be braided, interlaced, or otherwise woven into the desired pattern. In at least some embodiments, the stent body 210 and/or the wire filament(s) 214 may include a super elastic and/or shape memory material. For example, the stent body 210 and/or the wire filament(s) 214 may include a nickel-titanium alloy.

The stent 200 may have multiple longitudinal channels 218 formed along the outer surface of the stent body 210. Each of the longitudinal channels 218 may extend and run substantially along the longitudinal length of the stent body 210, between the first end 206 and the second end 202. However, in certain embodiments, the channels 218 may also extend only partially along the longitudinal length of the stent 200. As shown, four channels 218 may be provided along the stent body 210 of the stent 200. Other numbers of channels may also be utilized as disclosed herein. The shape of the channels 218 is depicted in the cross-sectional view of the second end 202 of the stent 200 illustrated in the upper left portion of FIG. 2. Each of the channels 218 may resemble a C-shape structure, extending longitudinally along the stent 200. This is just an example. Other suitable shapes for the channels 218 may also be contemplated, such as, rectangular, triangular or an irregular shape. Further, each channel 218 may extend radially inwards to a predetermined depth, from the stent body 210 of the stent 200.

The channels 218 may be configured to drain fluid out of a constriction portion of a target site (which may be the pancreatic duct 16 or the bile duct 18 shown in FIG. 1. More particularly, the channels 218 may allow side branches off of the pancreatic duct 16 or the bile duct 18 to be drained. For example, channels 218 may define a space between the outer surface of the stent body 210 and the body lumen where fluid may pass. Thus, fluid coming from side branches along the pancreatic and/or bile duct may flow into the channels 218, along the stent body 210, and ultimately into the duodenum. This may include the fluid passing through openings in the stent body 210 or along the channels 218 directly into the duodenum.

Accessing a target location within the biliary and/or pancreatic tree may incorporate use of an endoscope to position the stent 200 at the target location. For example, an endoscope may be advanced into a body lumen to a position adjacent to a target location. In certain embodiments, the target location may be the common bile duct 18 or the pancreatic duct 16 (shown in FIG. 1) of the biliary tree. Specifically, the endoscope may be advanced through the duodenum 12 to a position adjacent to the ampulla of Vater 14. When so positioned, the stent 200 may be passed through the endoscope towards the desired target. Depending on the location of the constricted area, the stent 200 may be advanced through the endoscope so that the second end 202 of the stent 200 is disposed along the constricted areas in the bile duct 18 and/or the pancreatic duct 16 of the patient's body.

Figure 3:
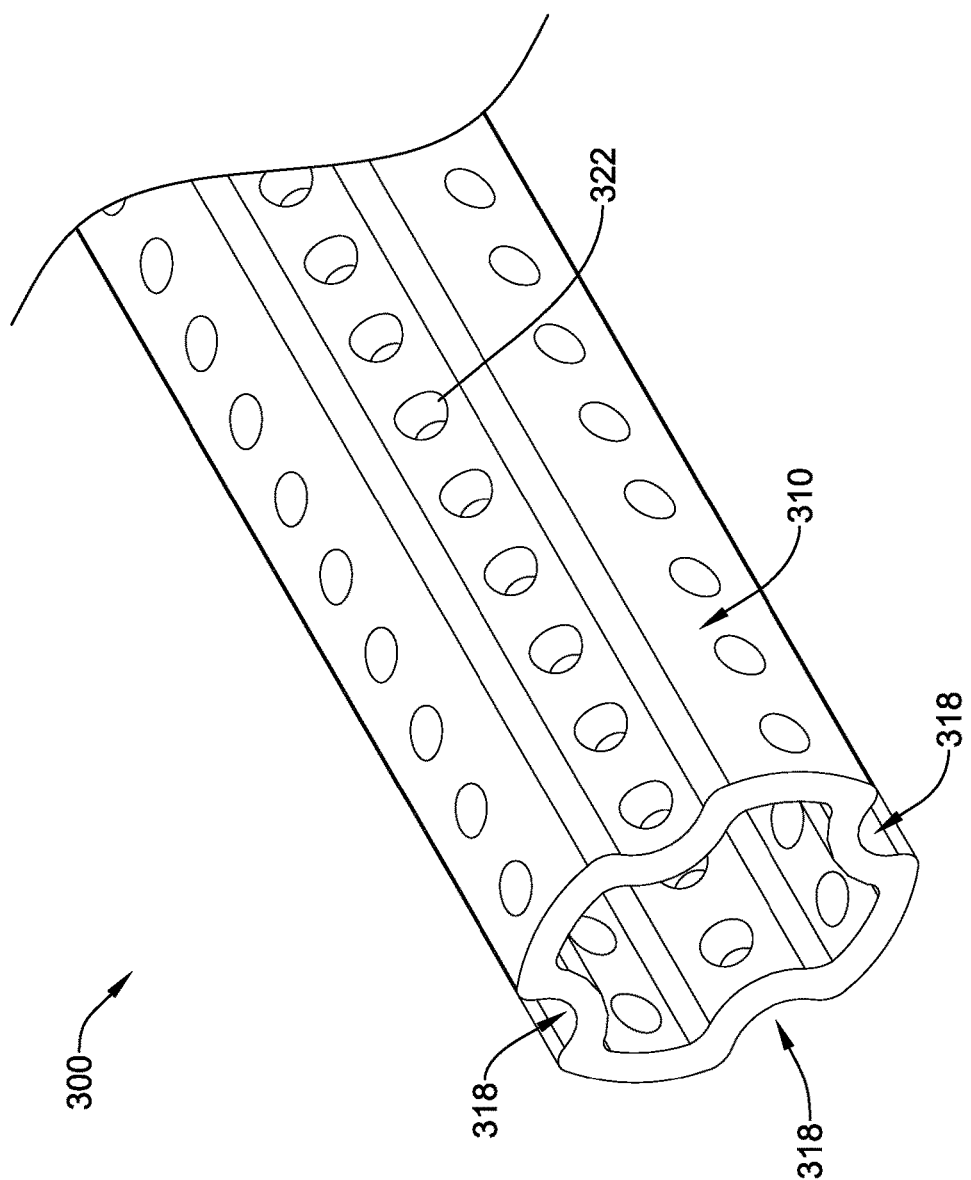
FIG. 3 is a perspective view of a portion of another example stent.

FIG. 3 illustrates a portion of another example stent 300 that may be similar in form and function to other stents disclosed herein. This figure illustrates another variation contemplated for the stents disclosed herein. For example, rather than being formed from a braid or mesh of wire filament(s), stent 300 may be formed from a tubular member 310 such as a metallic and/or polymeric tube. Tubular member 310 may be formed by extruding, molding, casting, or in any other suitable manner. In at least some embodiments, the central lumen of the tubular member 310 may have a shape corresponding to the outer profile of the tubular member 310, as shown. A plurality of openings 322 may be formed in the tubular member 310. In at least some embodiments, the openings 322 may be formed by laser cutting the tubular member 310. This is just an example. Other methods may be used to form the openings 322. In some embodiments, the tubular member may lack openings 322. Stent 300 may also include a plurality of channels 318. The channels 318 may be used, for example, to aid in the drainage of side branches off of the pancreatic duct (and/or other ducts) in a manner similar to channels 218.

Figure 4:
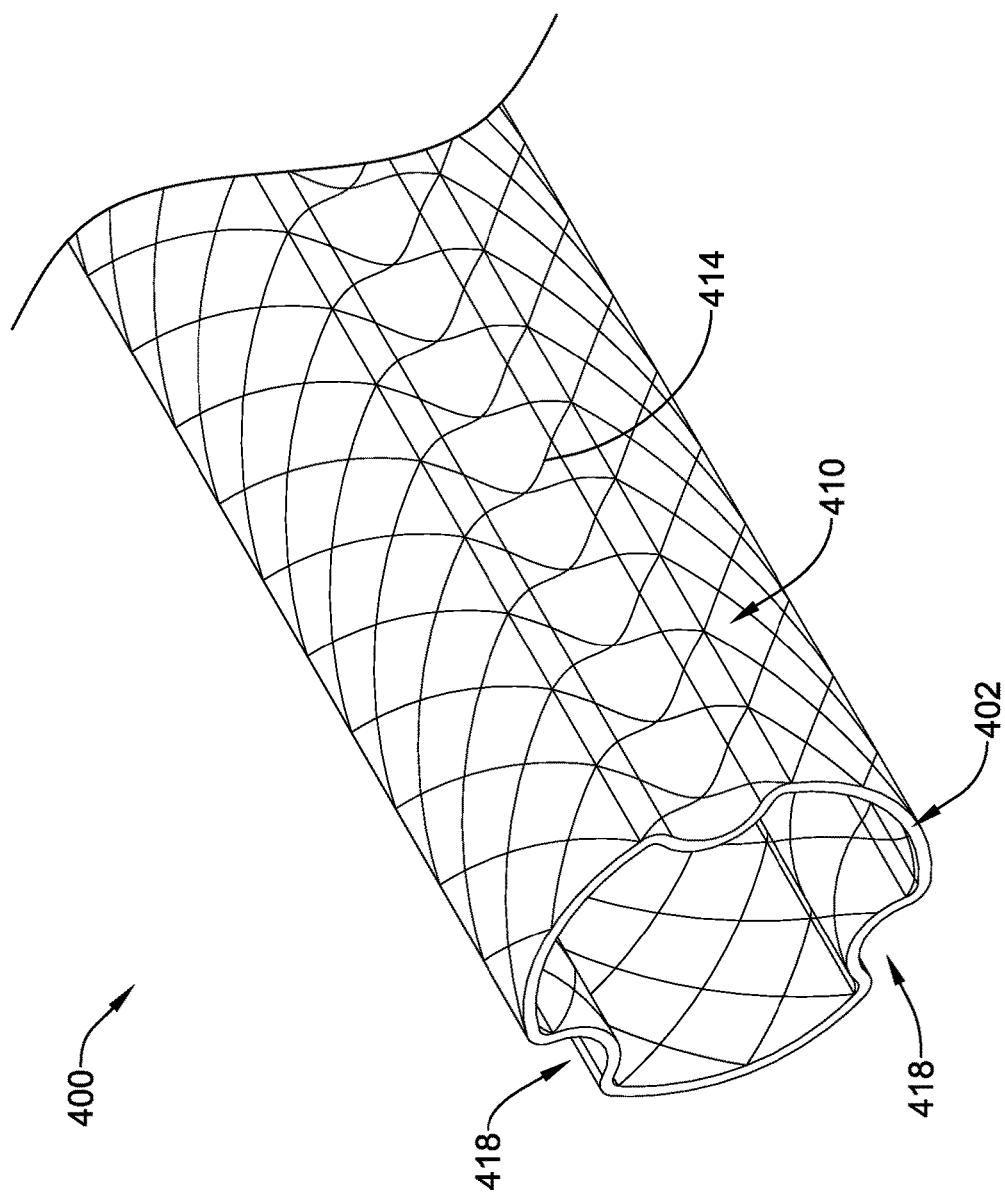
FIG. 4 is a perspective view of a portion of another example stent.
Figure 5:
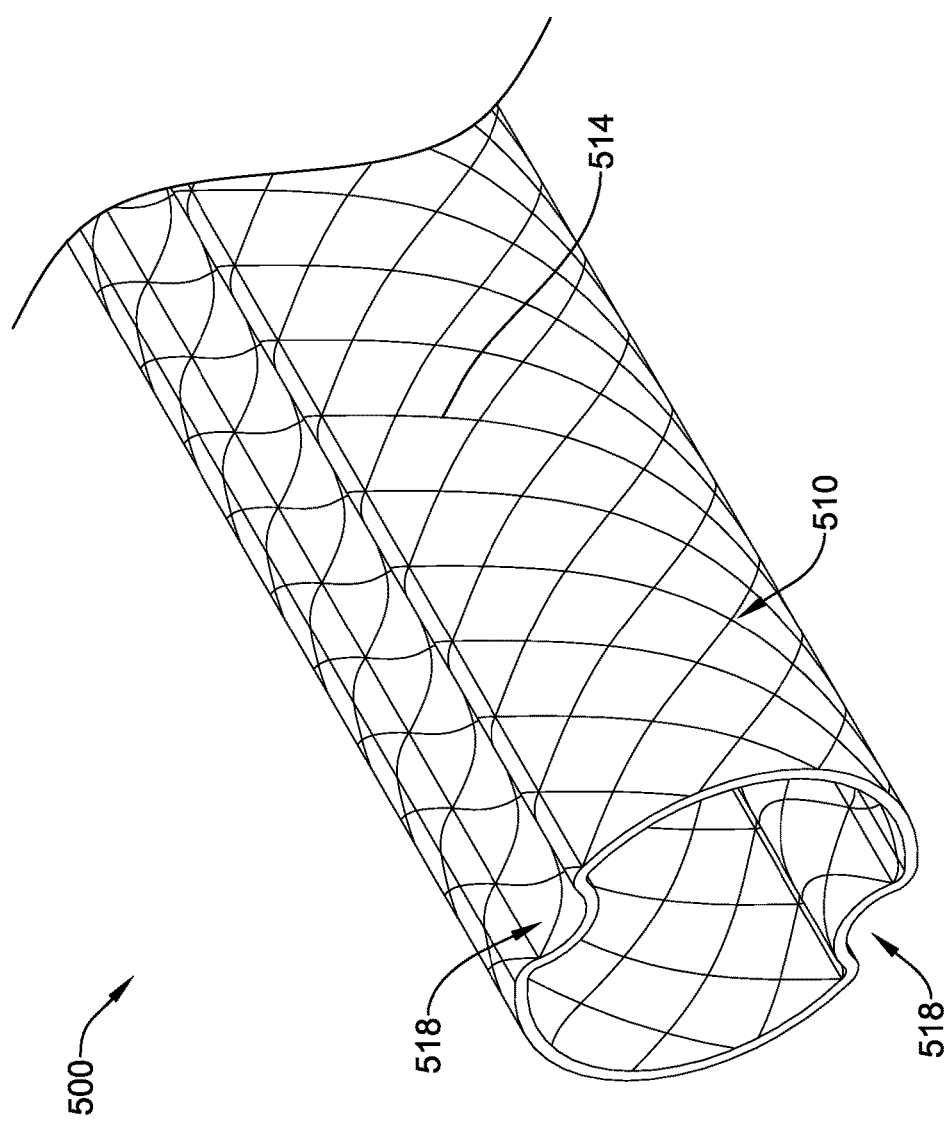
FIG. 5 is a perspective view of a portion of another example stent.

Numerous other variations are contemplated for the stents disclosed herein. As alluded to above, the number of channels may vary. For example, FIG. 4 illustrates a stent 400 formed from one or more wire filaments 414 and having end 402. In this example, the stent 400 has three channels 418 formed therein. Similarly, FIG. 5 illustrates stent 500 including a stent body 510 formed from one or more wire filaments 514. In this example, the stent 500 has two channels 518. Collectively, these figures illustrate that essentially any suitable number of channels may be utilized for the various stents disclosed herein including one channel, two channels, three channels, four channels, five channels, six channels, seven channels, eight channels, or the like.

Figure 6:
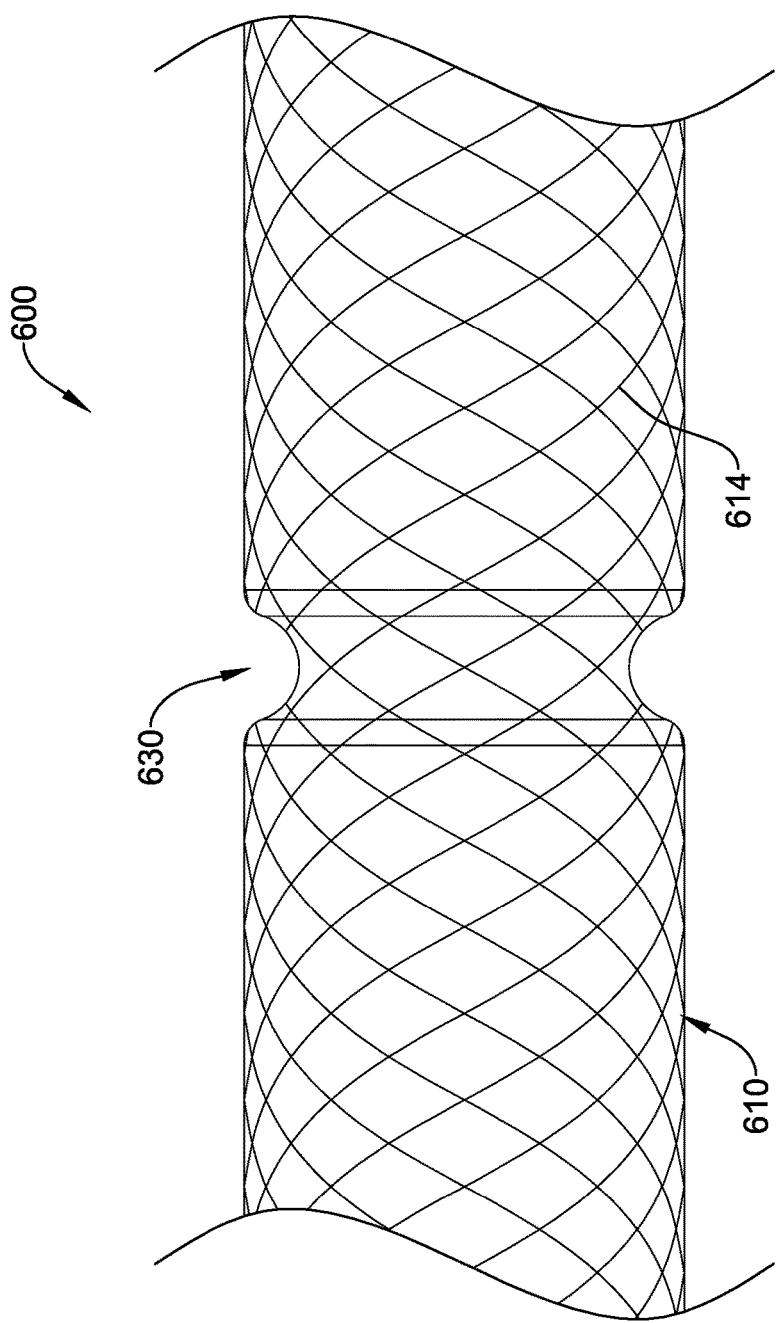
FIG. 6 is a side view of a portion of another example stent.

FIG. 6 illustrates a portion of another example stent 600 that may be similar in form and function to other stents disclosed herein. Stent 600 may include a stent body 610 formed from one or more wire filaments 614. This figure illustrates another variation contemplated for the stents disclosed herein. For example, in addition to the longitudinal channels disclosed herein, some stents like stent 600 may include one or more radial and/or circumferential channels 630. Circumferential channels 630 may provide another fluid path that allows fluids to travel circumferentially about the stent body 610. For example, some branch ducts may not completely align with the longitudinal channels 618 and, thus, in the absence of a circumferential channel 630 may not be efficiently drained. The presence of circumferential channels 630 may allow for more side branches to have access to fluid pathways for drainage. In doing so, fluid from the side branches may travel about the stent body 610 (via one of the circumferential channels 630) and into one or more of the longitudinal channels 618. Thus, circumferential channels 630 may further enhance the ability of stent 600 to drain fluids from side branches (e.g., side branches from the pancreatic duct).

Figure 7:
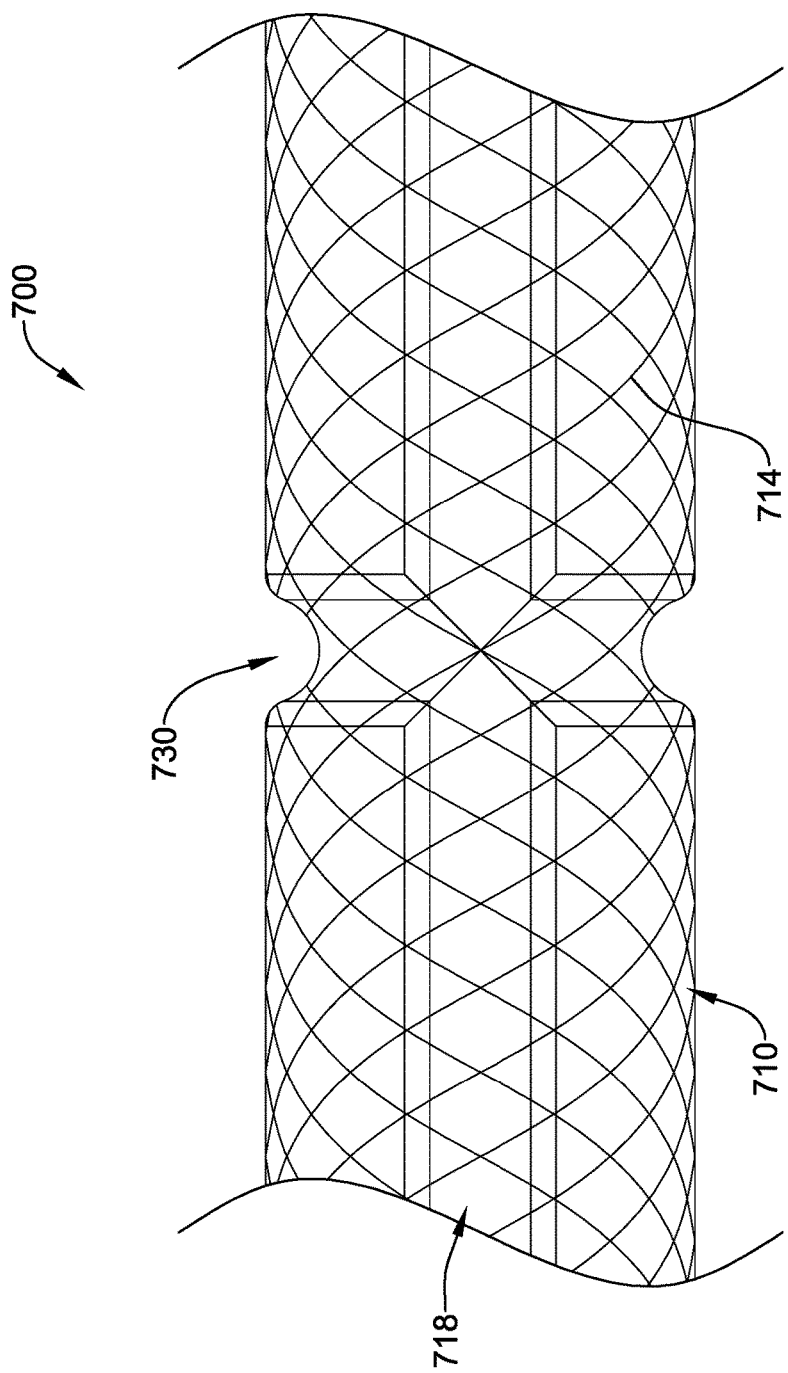
FIG. 7 is a side view of a portion of another example stent.

Some stents may include just longitudinal channels and some stents may include just circumferential channels. However, combinations may also be utilized. For example, FIG. 7 illustrates stent 700 formed from one or more wire filaments 714 and having outer surface 710. Stent 700 may include one or more longitudinal channels 718 and one or more circumferential channels 730. Channels 718/730 may aid in drainage of fluids in a manner similar to other channels disclosed herein.

Figure 8:
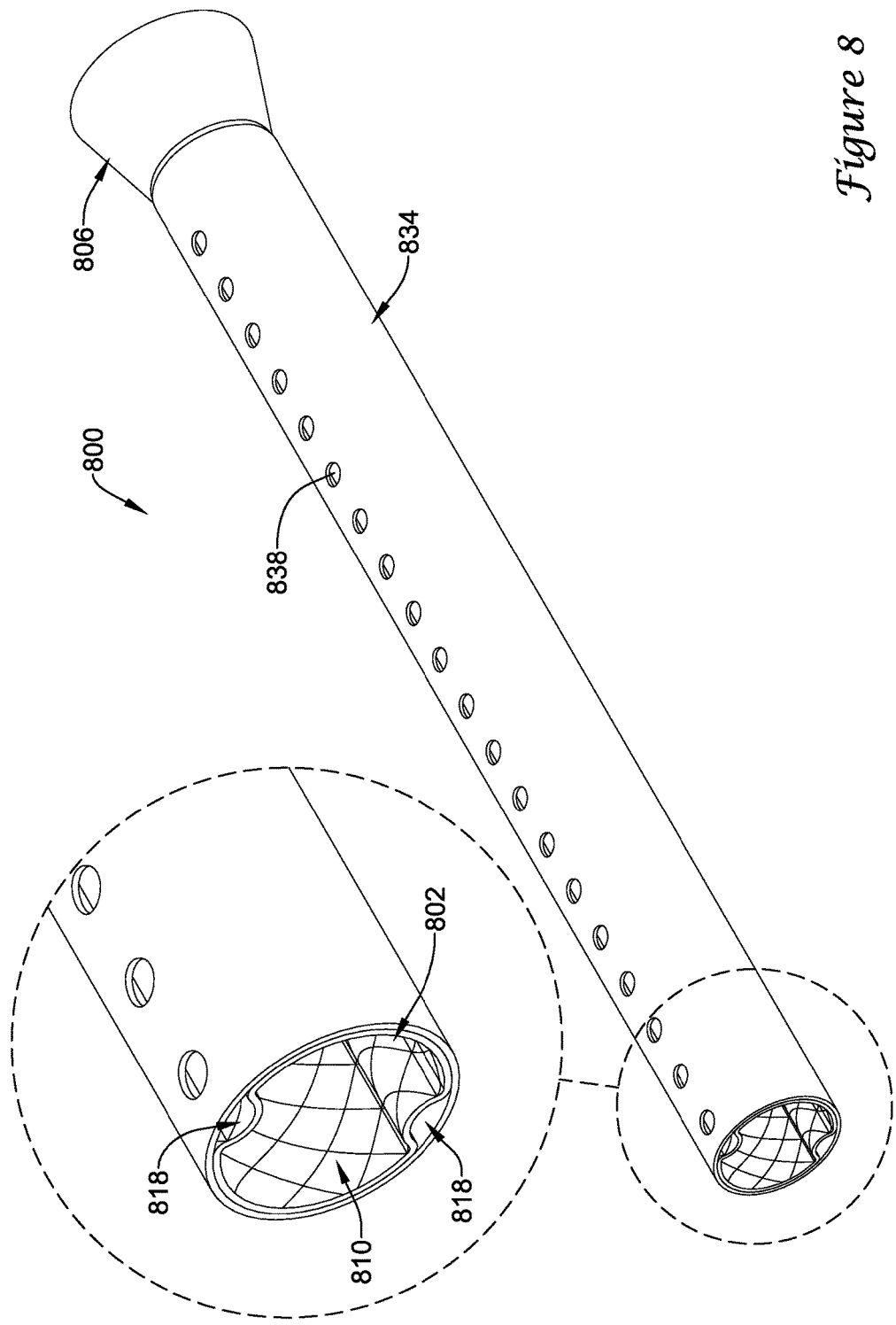
FIG. 8 is a perspective view of another example stent.

FIG. 8 illustrates a portion of another example stent 800 that may be similar in to form and function to other stents disclosed herein. Stent 800 may include a stent body 810 formed from one or more wire filaments similar to other stents disclosed herein and may include ends 802/806. Stent 800 may also include one or more channels 818.

Stent 800 may include a covering or coating 834 disposed over the stent body 810. The coating 834 may be applied to the stent 800. Alternatively, the coating may take the form of a polymeric sleeve, film, sheath, or tube that is disposed over and attached to the stent body 810. The coating 834 may have a plurality of openings 838 formed therein (e.g., after application of the coating 834). In at least some embodiments, the openings 838 may substantially align with channels 818. This may allow fluid to flow through the openings 838 and into the channels 818.

Figure 9:
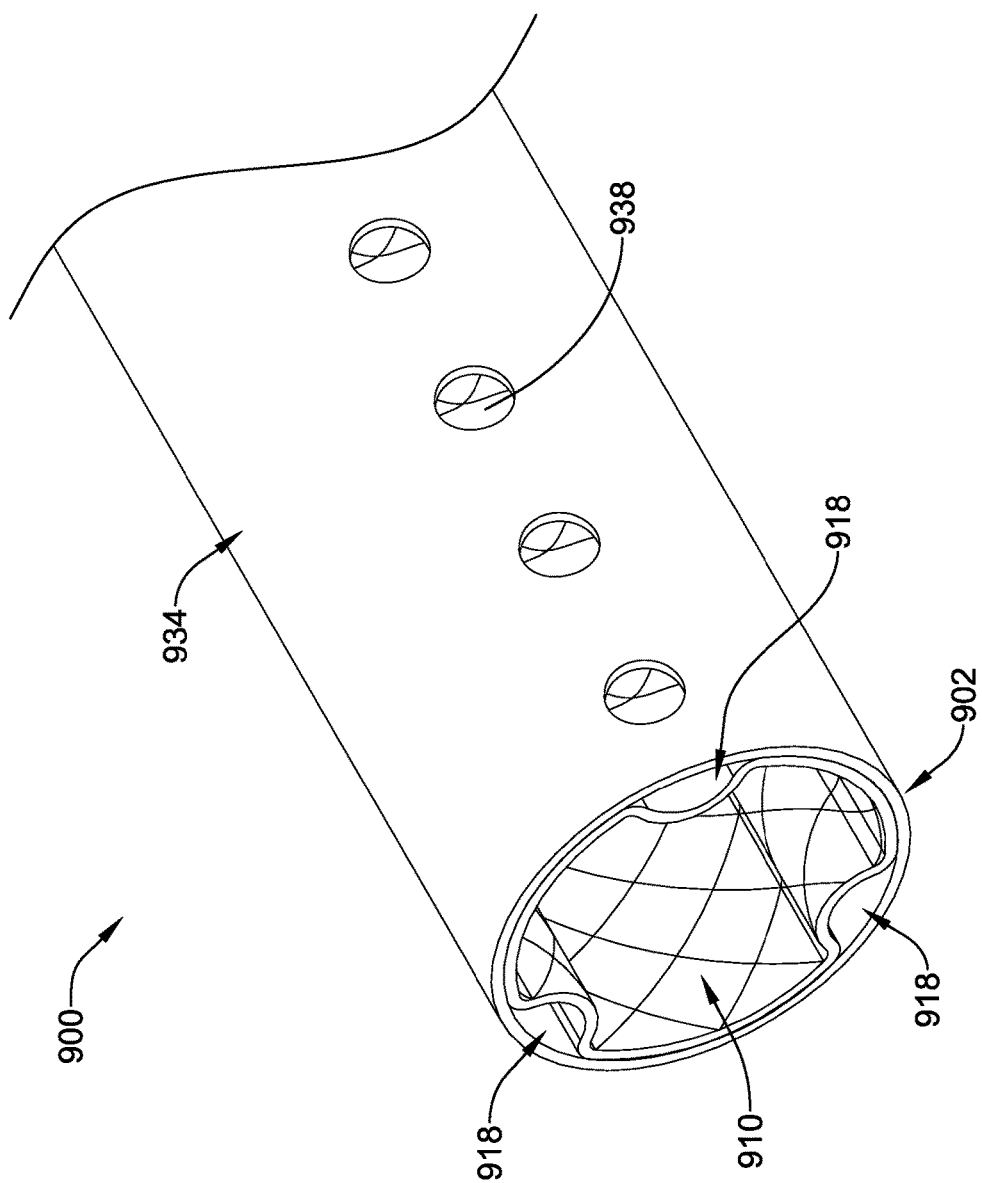
FIG. 9 is a perspective view of a portion of another example stent.
Figure 10:
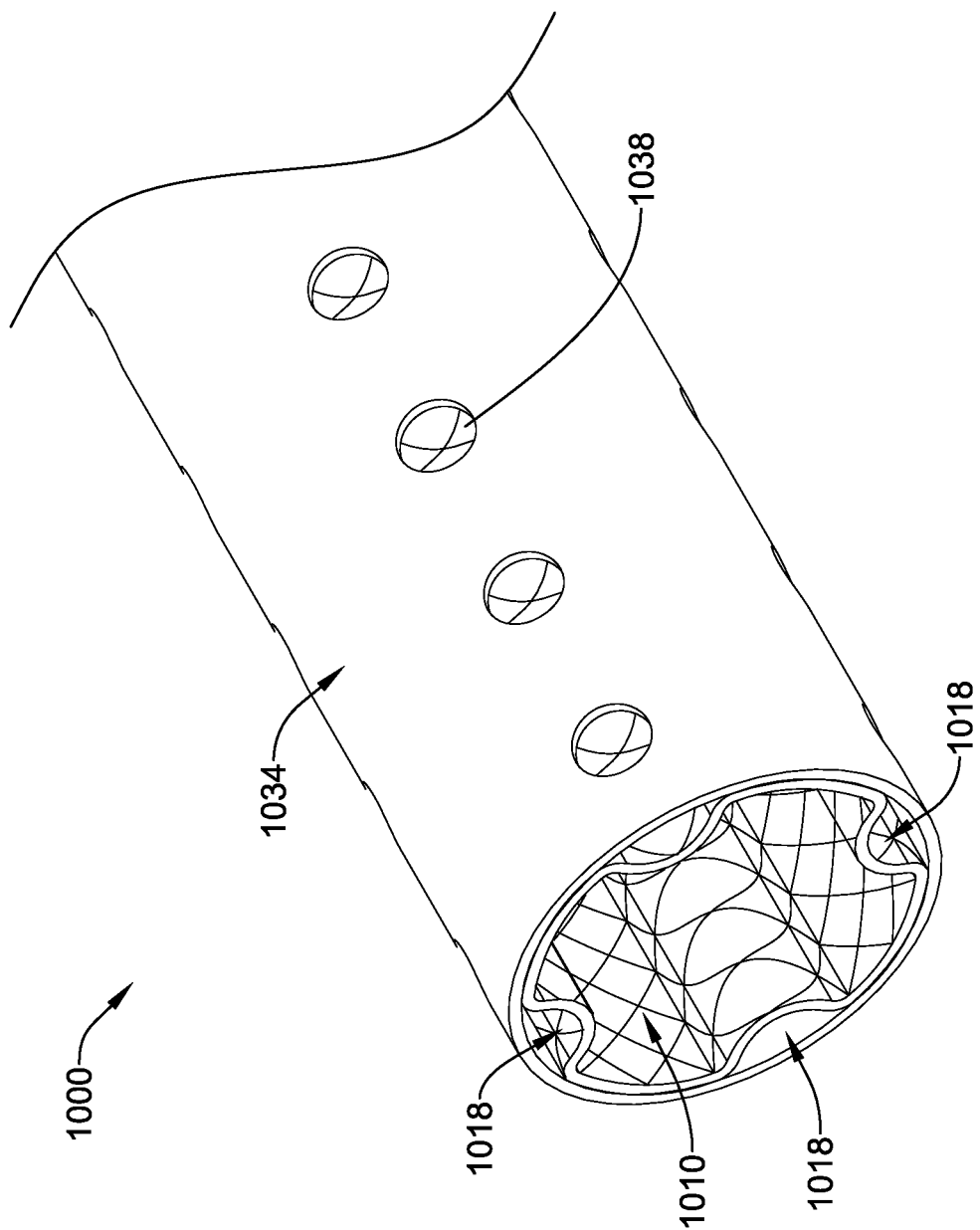
FIG. 10 is a perspective view of a portion of another example stent.

FIG. 9 illustrates a portion of another example stent 900 that may be similar in form and function to other stents disclosed herein. Stent 900 may include stent body 910. Coating 934 may be disposed on stent body 910. Coating 934 may have openings 938 formed therein. Openings 938 may be disposed along channels 918 formed in stent body 914. In this example, three channels 918 may be formed in stent body 910. Furthermore, FIG. 10 illustrates a portion of another example stent 1000 that may be similar in form and function to other stents disclosed herein. Stent 1000 may include stent body 1010. Coating 1034 may be disposed on stent body 1010. Coating 1034 may have openings 1038 formed therein. Openings 1038 may be disposed along channels 1018 formed in stent body 1010. In this example, four channels 1018 may be formed in stent body 1010. Collectively, these figures helps to illustrate that stents including a coating may also vary in the number of longitudinal channels formed therein. Thus, any suitable number of channels may be utilized in stent 800/900/1000 and other stents disclosed herein.

Figure 11:
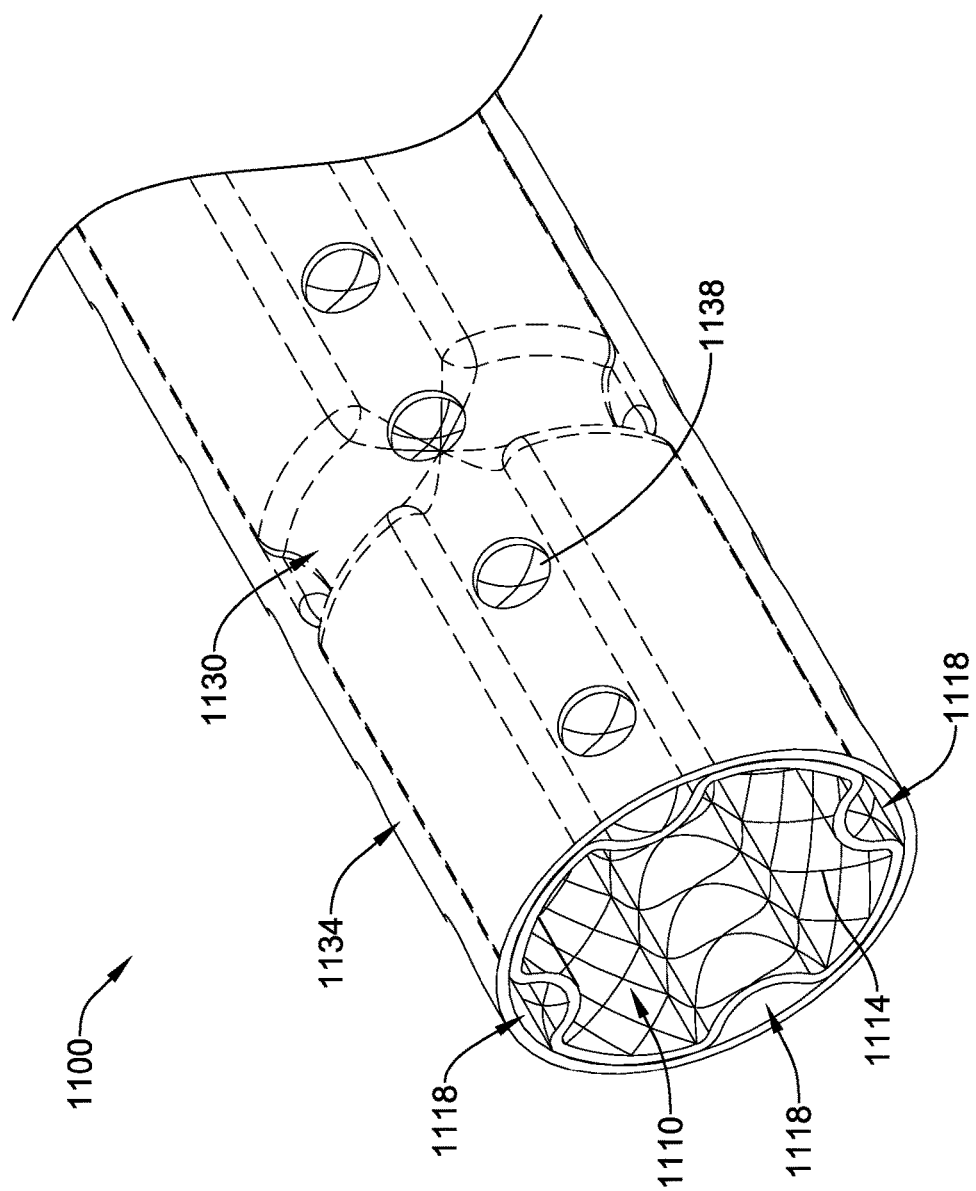
FIG. 11 is a perspective view of a portion of another example stent.

FIG. 11 illustrates a portion of another example stent 1100 that may be similar in form and function to other stents disclosed herein. Stent 1100 may include stent body 1110. Coating 1134 may be disposed on stent body 1110. Coating 1134 may have openings 1138 formed therein. Openings 1138 may be disposed along channels 1118 formed in stent body 1110. In this example, four channels 1118 may be formed in stent body 1110. In addition to channels 1118, stent body 1110 may also include one or more circumferential channels 1130. Collectively, channels 1118/1130 may aid in the drainage of fluid along the pancreatic and/or bile duct in a manner similar to other stents/channels disclosed herein.

The materials that can be used for the various components of stents disclosed herein may include those commonly associated with medical devices. For simplicity purposes, the following discussion makes reference to stent 200. However, this is not intended to limit the devices and methods described herein, as the discussion may be applied to other similar stents and/or components of stents or devices disclosed herein.

Stent 200 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of stent 200 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 200 in determining its location. Some examples of radiopaque materials can include, but are not limited to, gold, platinum, palladium, tantalum, tungsten alloy, polymer material loaded with a radiopaque filler, and the like.

In some embodiments, a degree of Magnetic Resonance Imaging (MRI) compatibility may be imparted into stent 200. For example, stent 200 may be made of a material that does not substantially distort the image and create substantial artifacts (i.e., gaps in the image). Certain ferromagnetic materials, for example, may not be suitable because they may create artifacts in an MRI image. Stent 200 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of draining fluid along a pancreatic and/or bile duct, the method comprising:
    inserting a stent through a duodenum and into the pancreatic and/or bile duct of a patient, the stent including a tubular member having a first end, a second end opposite the first end, an outer surface, and an inner surface defining a lumen extending through the tubular member from the first end to the second end, wherein the tubular member includes a flared region extending to the first end of the tubular member, wherein the tubular member is formed of one or more wire filaments that are woven together and includes a longitudinal channel formed in the outer surface by displacing the one or more wire filaments radially inward;
    positioning the stent across a side branch of the pancreatic and/or bile duct such that the first end including the flared region is positioned in the duodenum proximal of the side branch and the distal end is distal of the side branch and the longitudinal channel defines a space between an exterior of the stent and a luminal surface of the pancreatic and/or bile duct; and
    draining fluid from the side branch proximally along the exterior of the stent in the longitudinal channel and into the duodenum.

2. The method of claim 1, wherein the tubular member includes a longitudinal ridge formed in the inner surface by the displacement of the one or more wire filaments radially inward to form the longitudinal channel.

3. The method of claim 1, wherein the tubular member includes a cylindrical region adjacent to the flared region, wherein the cylindrical region extends to the second end of the tubular member.

4. The method of claim 3, wherein the longitudinal channel only extends along the cylindrical region of the tubular member such that the flared region is devoid of the longitudinal channel.

5. The method of claim 1, further comprising:
    draining fluid from the pancreatic duct through the lumen of the tubular member into the duodenum of the patient.

6. The method of claim 1, wherein the stent further comprises a covering disposed on the tubular member.

7. The method of claim 1, wherein the tubular member has a length measured from the first end to the second end, and wherein the longitudinal channel extends along a majority of the length of the tubular member.

8. A method of draining fluid along a biliary and/or pancreatic tract, the method comprising:
    disposing a stent within the pancreatic and/or bile duct such that a first end including a flared region of the stent is disposed within a duodenum of the patient and a second end of the stent extends into the biliary and/or pancreatic tract of the patient distal of a side branch, the stent including a braided tubular structure having an outer surface with a longitudinal channel formed therein, the longitudinal channel defining a space between an exterior of the stent and a luminal surface of the pancreatic and/or bile duct; and
    draining fluid from the side branch proximally along the exterior of the stent in the longitudinal channel and into the duodenum.

9. The method of claim 8, wherein the stent includes a cylindrical region adjacent to the flared region, wherein the cylindrical region extends to the second end of the stent.

10. The method of claim 9, wherein the longitudinal channel only extends along the cylindrical region of the stent such that the flared region is devoid of the longitudinal channel.

11. The method of claim 8, wherein the stent has a length measured from the first end to the second end, and wherein the longitudinal channel extends along a majority of the length of the stent.

12. A method of draining fluid along a pancreatic and/or bile duct, the method comprising:
    inserting a stent through a duodenum and into the pancreatic and/or bile duct of a patient, the stent including a first end, a second end opposite the first end, an outer surface, and an inner surface defining a lumen extending through the stent from the first end to the second end, wherein the stent includes a flared region extending to the first end of the stent, wherein the stent includes a braided tubular member formed of a plurality of wire filaments that are woven together; wherein the stent includes a plurality of longitudinal channels formed in the outer surface by displacing the plurality of filaments radially inward; and positioning the stent across a side branch of the pancreatic and/or bile duct such that the first end including the flared region is positioned in the duodenum proximal of the side branch and the distal end is distal of the side branch and the plurality of longitudinal channels each define a space between an exterior of the stent and a luminal surface of the pancreatic and/or bile duct; and draining fluid from the side branch proximally along the exterior of the stent in the plurality of longitudinal channels and into the duodenum.

13. The method of claim 12, wherein the stent includes a cylindrical region adjacent to the flared region, wherein the cylindrical region extends to the second end of the stent.

14. The method of claim 13, wherein the plurality of longitudinal channels only extend along the cylindrical region of the stent such that the flared region is devoid of the plurality of longitudinal channels.

15. The method of claim 12, wherein the braided tubular member has a length measured from the first end to the second end, and wherein the plurality of longitudinal channels extend along a majority of the length of the braided tubular member.

16. The method of claim 12, wherein the stent further comprises a covering disposed on the braided tubular member.

* * * * *